United States Patent [19]

Bambury et al.

[11] Patent Number: 4,719,248

[45] Date of Patent: Jan. 12, 1988

[54] ULTRAVIOLET BLOCKING AGENTS FOR CONTACT LENSES

[75] Inventors: Ronald E. Bambury, Fairport, N.Y.; Joon S. Park, Arlington, Tex.; Dong J. Choo, Seoul, Rep. of Korea

[73] Assignee: Bausch & Lomb Incorporated, Rochester, N.Y.

[21] Appl. No.: 763,947

[22] Filed: Aug. 8, 1985

[51] Int. Cl.$^4$ .......................... G02B 1/04; G02C 7/04
[52] U.S. Cl. ...................... 523/108; 350/1.1; 350/448; 351/160 R; 351/163; 351/167; 523/106; 526/261; 526/263
[58] Field of Search .................. 523/106, 108; 522/14, 522/26, 53; 351/160 R, 163, 167; 350/1.1, 448; 526/263, 261

[56] References Cited

U.S. PATENT DOCUMENTS

| | | | |
|---|---|---|---|
| 2,241,415 | 5/1941 | Moulton | 351/160 |
| 3,171,869 | 3/1965 | Weinberg | 88/54.5 |
| 3,186,968 | 6/1965 | Fertig et al. | 260/47 |
| 3,189,914 | 6/1965 | Gusewitch et al. | 351/160 |
| 3,328,491 | 6/1967 | Fertig et al. | 260/901 |
| 3,340,231 | 9/1967 | Fertig et al. | 260/47 |
| 3,365,421 | 1/1968 | Horton et al. | 260/47 |
| 3,399,173 | 8/1968 | Heller et al. | 260/47 |
| 3,408,429 | 10/1968 | Wichterle | 351/160 |
| 3,476,499 | 11/1969 | Wichterle | 351/160 |
| 3,985,697 | 10/1976 | Urbach | 523/106 |
| 4,094,756 | 6/1978 | Taylor | 522/53 |
| 4,157,892 | 6/1979 | Tanaka et al. | 351/162 |
| 4,304,895 | 12/1981 | Loshaek | 351/160 H |
| 4,390,676 | 6/1983 | Loshaek | 351/160 H |
| 4,434,035 | 2/1984 | Eichler et al. | 522/53 |
| 4,505,794 | 3/1985 | Krita et al. | 522/53 |
| 4,518,473 | 5/1985 | Jacobine | 522/14 |
| 4,528,311 | 7/1985 | Beard et al. | 351/160 H |

FOREIGN PATENT DOCUMENTS 885986  1/1962  United Kingdom .

OTHER PUBLICATIONS

Yates et al., J. Org. Chem., 49, 3349–56 (1984).
Pappas (ed.), *UV Curing: Science and Technology*, (Technology Marketing, Stanford 1978), Chapter 4.
Clarke et al., J. Macromol. Sci. Chem., A14(1), 66–79 (1980).
Aldrich et al., J. Radiat. Curing 11, 10–17 (1984).
Van Landuyt, J. Radiat. Curing, 11, 4–8 (1984).
Chylack, Opthamology, 91, 596 (1984).
Osborne, J. Radiat. Curing, 3, 2–11 (1976).
Pappas (ed.), *UV Curing: Science and Technology*, (Technology Marketing, Stanford 1978), pp. 2–22 and 79–95.
Belusa et al., Chem. Zvesti 28, 672–679 (1974).
Nir et al., "Functional Polymers", Journal of Polymer Science: Polymer Chemistry Edition, 20:2735–2754 (1982).
Mandell, *Contact Lens Practice: Basic and Advanced* (Charles C. Thomas 1965) pp. 234–239.
Xi et al., "Functional Polymers", Polymer Bulletin, 11:329–335 (1984).
Dexter, "UV Stabilizers", Kirk-Othmer Encyclopedia of Chemical Technology 23: 615–627 (3d. ed. 1983).

*Primary Examiner*—Allan M. Lieberman
*Attorney, Agent, or Firm*—Craig E. Larson; Christopher E. Blank; Bernard D. Bogdon

[57] ABSTRACT

Novel ultraviolet absorbing compounds useful in contact lenses and methods for curing contact lenses containing UV absorbers are disclosed.

9 Claims, 2 Drawing Figures

ULTRAVIOLET BLOCKING AGENTS FOR CONTACT LENSES

BACKGROUND OF THE INVENTION

1. Field of the Invention

The present invention relates to compositions that absorb ultraviolet (UV) light and the use of such compositions in contact lenses.

2. Description of the Prior Art

It is well known that sunlight can result in damage to the human eye, especially in connection with the formation of cataracts. The fraction of sunlight of most concern is the long wave or near ultraviolet range, which is characterized by wavelength of 300-400 nanometers (nm). This band of ultraviolet radiation is known to cause damage to the eye by inducing chemical changes in the lens and retina. Though short wavelength light with wave lengths below 300 nm. typically does not reach the earth's surface because of the atmospheric ozone layers, most of the long wave ultraviolet radiation in the 300-400 nm. range is capable of penetrating to the surface of the earth.

The problem of eye damage caused by the penetrating long wave ultraviolet radiation is especially acute in aphakic patients. Aphakic patients have lost their natural lens, which is the primary ultraviolet filter in the eye. Without this natural UV filter, aphakic patients are far more susceptible to the photochemical damage that long range ultraviolet light can induce.

A variety of compositions are known in the art that absorb at least part of the spectrum of ultraviolet light. Examples of such ultraviolet absorbers or blockers are disclosed in Xi et al., "Functional Polymers", Polymer Bulletin 11: 329-335 (1984); Dexter, "UV Stabilizers", Kirk-Othmer Encyclopedia of Chemical Technology 23: 615-627 (3d ed. 1983); Nir et al., "Functional Polymers", Journal of Polymer Science: Polymer Chemistry Edition 20: 2735-2754 (1982); United Kingdom Patent Specification No. 885,986; and U.S. Pat. Nos. 3,399,173 and 3,365,421.

In the context of protecting the human eye, it is known that UV absorbers can be incorporated into spectacles to prevent ultraviolet light from reaching the eye, as disclosed in U.S. Pat. No. 3,171,869. Similarly, it is well known in the art to incorporate ultraviolet blocking compositions into contact lenses, as disclosed in Mandell, *Contact Lens Practice: Basic and Advanced* (Charles C. Thomas 1965) 234-39; and U.S. Pat. Nos. 2,241,415; 3,189,914; 3,476,499; 4,157,892, 4,304,895; and 4,390,676. Such UV absorbers are typically copolymerized with the base polymer used to manufacture the lens in order to eliminate any possible toxicity or migration problems, as disclosed in U.S. Pat. Nos. 3,186,968; 3,328,491; and 3,340,231. Contact lenses may be formed from such polymers according to various methods well known in the art, such as the spincasting method described in U.S. Pat. No. 3,408,429.

One problem that has arisen in connection with commercial contact lenses containing UV blockers is that they tend to appear yellow. Such yellow appearing contact lenses are not esthetically pleasing to the user and thus present a significant commercial problem. Therefore, there is a need for a UV absorbing composition suitable for use in contact lenses that will not cause the contact lenses to appear yellow and yet will block out as much of the potentially harmful radiation as possible.

An additional problem that has arisen in the curing of materials containing UV absorbing pigments and dyes is that such pigments and dyes adversely affect the curing of such materials with UV radiation. Pappas (ed.), *UV Curing: Science and Technology*, (Technology Marketing, Stanford 1978), pp. 2-22, 79-95. Therefore, there is a need for a curing method that will avoid such problems in the curing of contact lenses containing UV absorbing compositions.

SUMMARY OF THE INVENTION

It is an object of the present invention to provide novel UV blocking compounds.

It is a further object of the present invention to provide novel UV blocking compounds that can be incorporated into contact lenses in order to prevent UV damage to the lens and retina.

It is an additional object of the present invention to provide contact lenses including novel UV blocking compounds that are not yellow in appearance.

It is a specific object of the present invention to provide UV blocking compounds having the following formula:

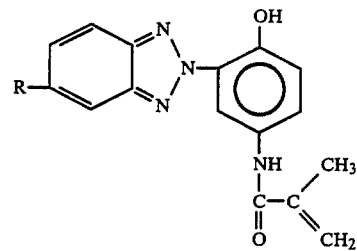

where R is either Cl or OCH$_3$. These compounds are capable of absorbing a substantial amount of the long range UV radiation having wavelengths between 300 and 400 nm. In addition, when these compounds are incorporated into contact lenses in sufficient amounts to absorb UV light, the resulting lenses do not appear yellowed. It is believed that this lack of yellowing is due to the fact that the novel UV absorbing compounds of the present invention absorb very little light having wavelengths above 400 nm. It is believed that absorption of light above 400 nm. results in the objectionable yellowing found in conventional UV absorbing contact lenses.

It is another object of the present invention to provide a method of curing contact lens materials containing a UV absorbing composition that avoids the problems of curing with UV radiation.

It is a further specific object of the present invention to provide a method of polymerizing a monomeric contact lens material that contains a UV absorber. The cure is obtained by incorporating both a photoinitiator and a proton transfer agent into the contact lens material and then irradiating the resulting material under visible light for a sufficient amount of time to cure the lens material.

Further objects and embodiments will be made clear in the following description of the preferred embodiments and claims.

DESCRIPTION OF THE PREFERRED EMBODIMENT

The novel ultraviolet absorbing or blocking compounds of the present invention are 2-(2-hydroxy-5-methacrylamidophenyl)-5-chlorobenzotriazole (the "chloro compound") and 2-(2-hydroxy-5-methacrylamidophenyl)-5-methoxybenzotriazole (the "methoxy compound"). The method of synthesis of these compounds is similar to the method disclosed in Belusa et al., Chem. Zvesti, 28, 672–679 (1974) for another benzotriazole. The overall synthetic scheme is depicted below:

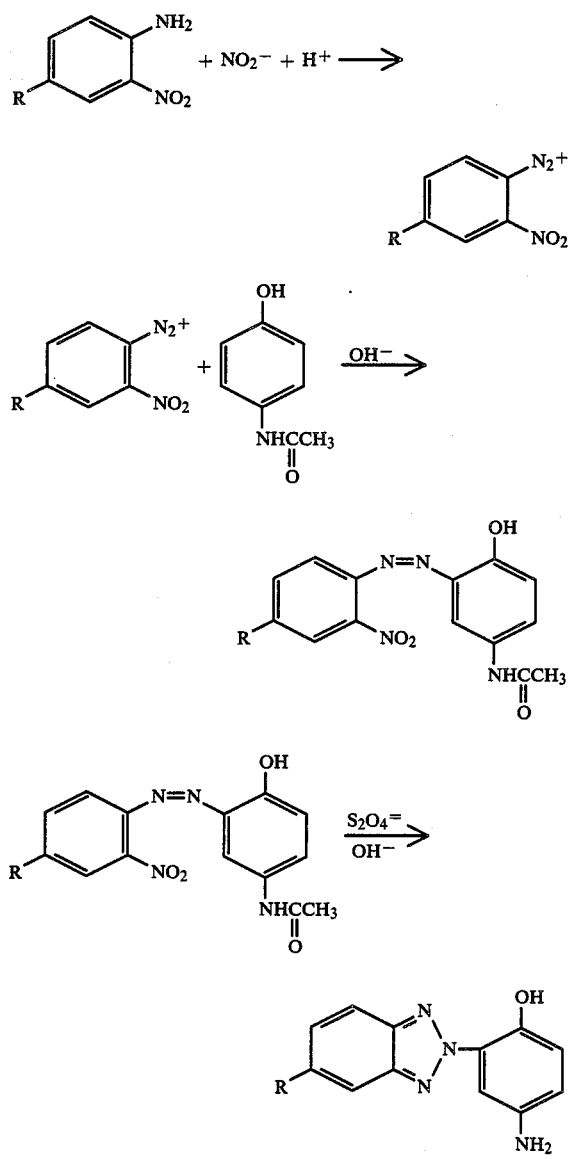

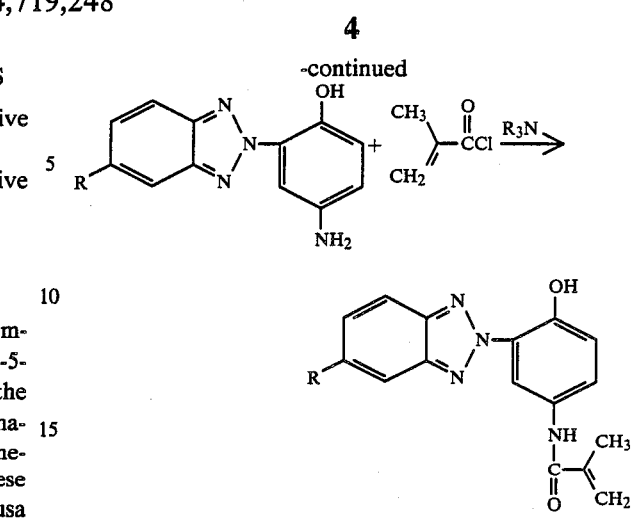

where R is Cl or $OCH_3$.

The first step of the sequence is a standard diazotization and the diazonium salt is used immediately without isolation in the next step. Coupling of the diazonium salt with the acetamidophenol is carried out in aqueous solution to give the highly colored azo compound. One attempt to carry out this reaction in pyridine was not successful. Next, the azo compound is reductively cyclized with dithionite to yield the oxygen sensitive aminophenol-benzotriazole derivative and concurrently remove the acetyl protecting group. The product is collected by filtration, under nitrogen and dried under vacuum. Once dry, the material is not quite as oxygen sensitive. The material is acylated with methacryloyl chloride using triethylamine as the proton acceptor. The overall yield of the sequence is approximately six percent.

Figure 1:
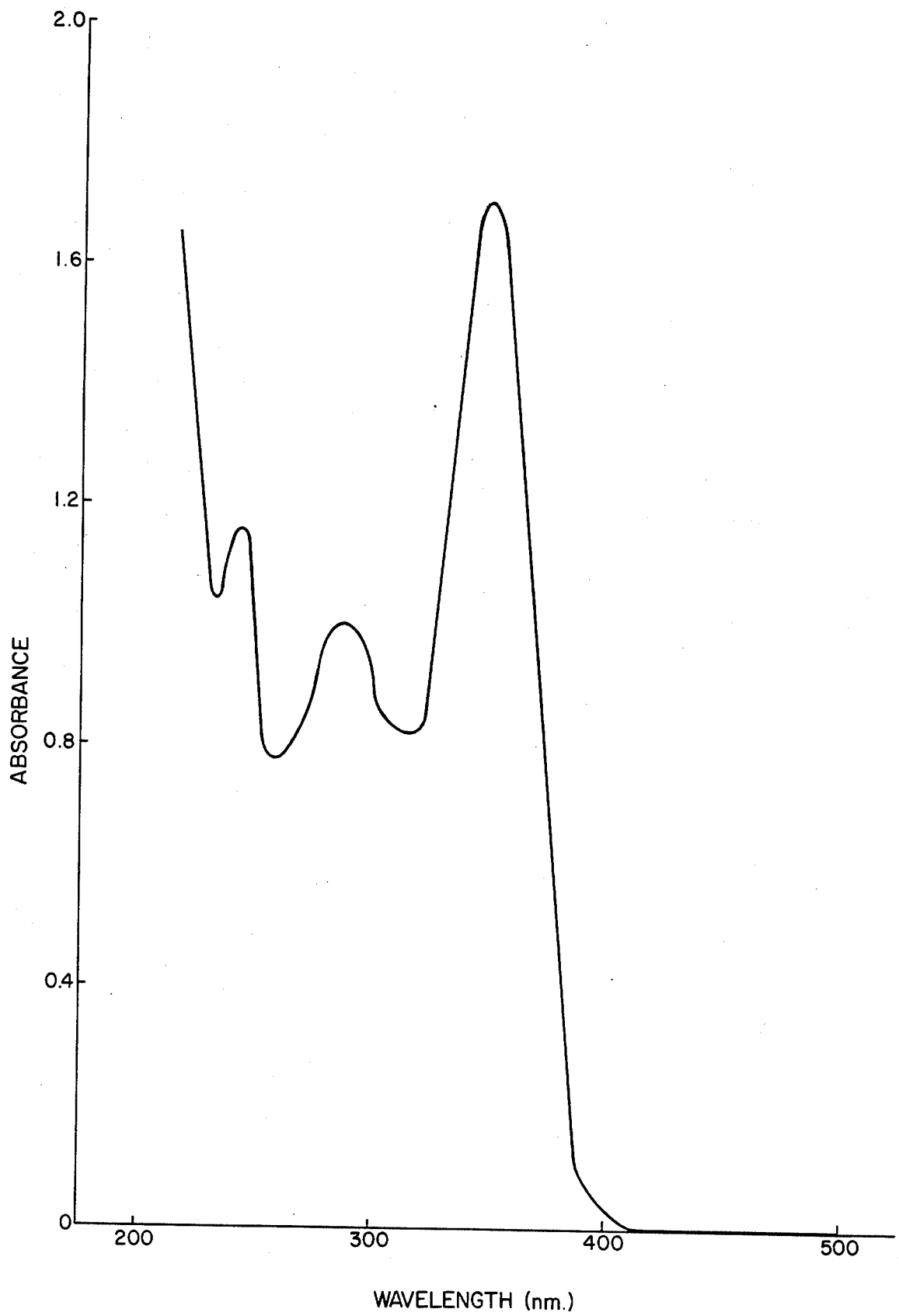
FIG. 1 is an ultraviolet spectrum of the inventive methoxy compound.
Figure 2:
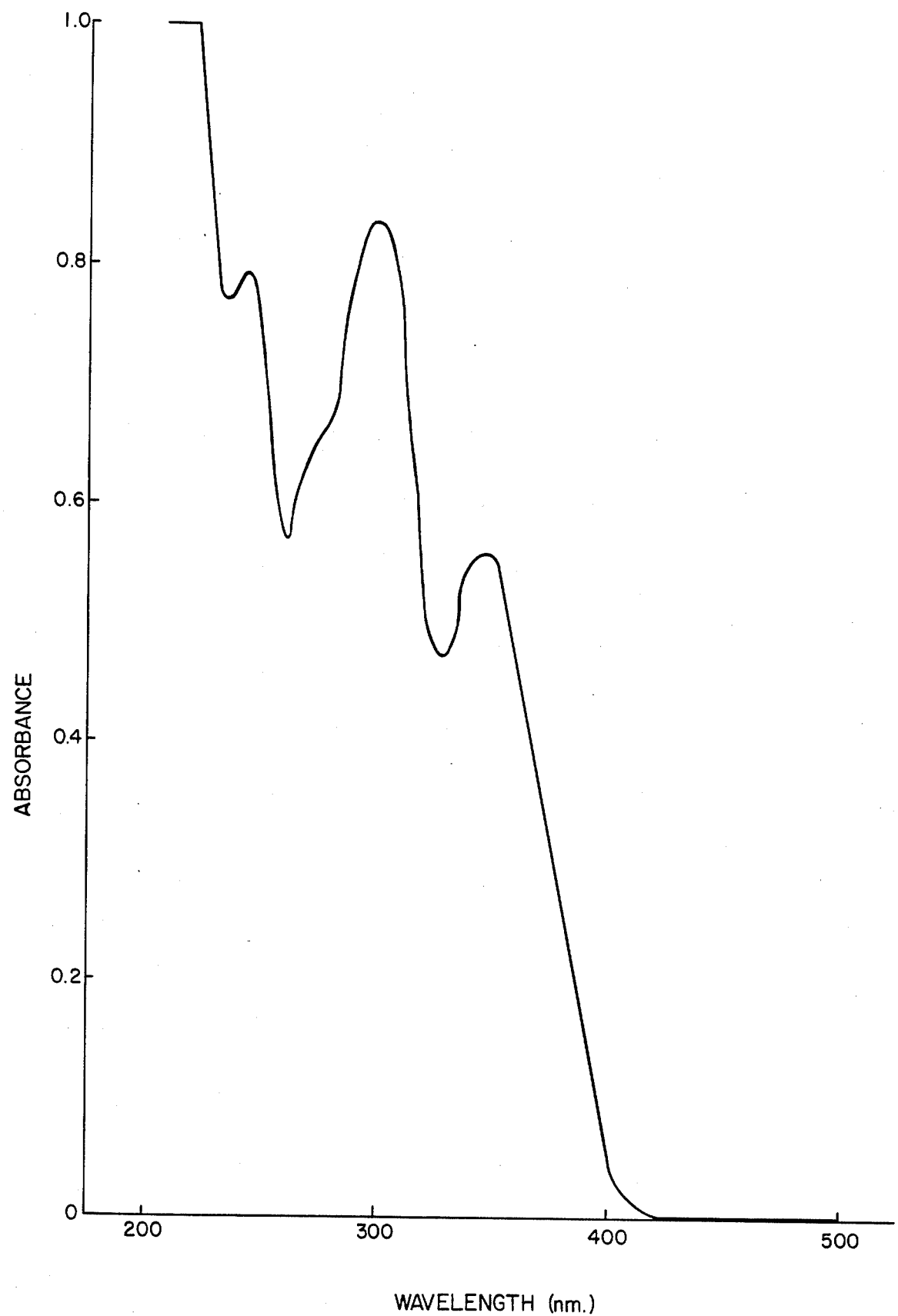
FIG. 2 is an ultraviolet spectrum of the inventive chloro compound.

The ultraviolet spectra of the inventive compounds are shown in FIG. 1 (where R=Cl) and FIG. 2 (where R=$OCH_3$). The spectra are characterized by strong UV absorption below 400 nm. This type of spectrum is nearly ideal for the type of UV blocking desired in contact lenses. It should be noted that the methoxy compound has slightly less absorption above 400 nm. and a more intense absorption peak at 380 nm. This indicates that the inventive methoxy compound may provide UV blocking below 400 nm. equivalent to that of the chloro compound, while imparting less of a visible yellow tint to contact lenses in which it is incorporated.

EXAMPLE 1

Synthesis of 2-(2-hydroxy-5-aminophenyl)-5-chlorobenzotriazole

To a cooled (0°–5° C.), well stirred suspension of 4-chloro-2-nitroaniline, 34.4 g. (0.2 mole) in 80 ml. of concentrated hydrochloric acid was added, dropwise, 18.0 g. (0.26 mole) of sodium nitrite in 10 ml. of water. The addition required approximately 30 minutes. After the addition was complete, the reaction mixture was filtered and the filtrate placed in an addition funnel containing approximately 100 g. of crushed ice. This solution was used immediately in the next step. The solution was added, dropwise, over 30 minutes to a well stirred suspension of 30.2 g. (0.2 mole) of p-acetamidophenol in 600 ml. of water containing 60 g. of sodium bicarbonate and 8 g. sodium hydroxide. The addition took about 20–30 minutes. The reaction was run most conveniently in a large beaker and small portions of ether were added to reduce foaming. The mixture was stirred for two hours and the dark red azo dye was collected by filtration and washed with a little water. The wet filter cake was suspended in 2,000 ml. of 5% sodium hydroxide and stirred well under nitrogen for 30 minutes. While maintaining a nitrogen atmosphere, 140 g. of $Na_2S_2O_4$ was added in portions over one hour. The mixture was then boiled for one hour, cooled and filtered under nitrogen. The filtrate was acidified, under nitrogen, to a pH of 5. The yellow-grey precipitate was collected by filtration under nitrogen and dried in a vacuum desiccator to give 20 g. (38% yield) crude benzotriazole.

EXAMPLE 2

Synthesis of 2-(2-hydroxy-5-methacrylamidophenyl)-5-chlorobenzotriazole

To 10.4 g. (0.04 mole) of 2-(2-hydroxy-5-aminophenyl)-5-chlorobenzotriazole and 4.1 g. triethylamine in 400 ml. methylene chloride (no preservative) was added at 0°-5° C., under nitrogen, with stirring, 4.2 g. methacryloyl chloride in 30 ml. methylene chloride. The dropwise addition required about 30 minutes. The mixture was stirred at 0°-5° C. for an additional 30 minutes and then at room temperature for one hour. The mixture was then washed with equal volumes of water, 5% hydrochloric acid and water. The organic phase was dried over magnesium sulfate and poured onto a 2" column of silica gel (120 g.) which had been slurry packed with methylene chloride. The column was eluted with methylene chloride and 100 ml. fractions were taken. The fractions were examined by thin layer chromatography (TLC) on silica gel plates using 1:5, ethyl acetate:chloroform as the developing solvent. The fractions containing the product (r.f. 0.36) were combined and evaporated. The residual solid was crystallized from ethanol to give 2.2 g. of product, m.p. 204°-205° C.

EXAMPLE 3

Synthesis of 2-(2-hydroxy-5-aminophenyl)-5-methoxybenzotriazole

The same general procedure as described in Example 1 was followed. To a stirred suspension of 16.8 g. of methoxynitroaniline in 60 ml. of concentrated hydrochloric acid was added over 0.5 hr., at 0°-5° C., a solution of 9.0 g. $NaNO_2$ in 30 ml. water. The solution of diazonium salt was filtered and placed in an addition funnel containing about 100 g. ice. The solution was added dropwise to 15 g. of p-acetamidophenol in 300 ml. water containing 4 g. NaOH and 45 g. $NaHCO_3$. Foaming was controlled by the periodic addition of ether. The mixture was stirred for one hour after the addition was completed and the azo dye collected by filtration. The dye was washed with water and used directly in next step. The azo dye was added to 1,200 ml. 5% NaOH solution and stirred for 20 minutes. The reaction mixture was then blanketed with nitrogen and 70 g. of $Na_2S_2O_4$ was added in small portions over one hour. The mixture was heated for one hour at reflux, cooled and filtered through celite. The product was precipitated under nitrogen by the addition of concentrated hydrochloric acid to a pH of 5. The yellow-brown precipitate was collected by filtration and dried in a vacuum desiccator (wt. 8.7 g.).

EXAMPLE 4

Synthesis of 2-(2-hydroxy-5-methacrylamidophenyl)-5-methoxybenzotriazole

To a stirred mixture of the methoxybenzotriazole (8.5 g., 0.033 mole) and 3.4 g. triethylamine in 300 ml. chloroform was added, dropwise, 3.4 g. methacryloyl chloride in 30 ml. chloroform. The addition was carried out at 0°-5° C. over 30 minutes. The mixture was stirred an additional 0.5 hr. at room temperature and washed with water, 5% hydrochloric acid and water. The organic phase was dried over magnesium sulfate and poured onto a 2" diameter column of silica gel which had been slurry packed with chloroform. The column was eluted with 200 ml. chloroform and then 9:1, chloroform:ethyl acetate. The fractions were monitored by TLC on silica gel plates using 9:1, chloroform:ethyl acetate. The fractions containing the component of rf. 0.55 were combined and evaporated and the residue crystallized from ethanol, wt. 1.9 g., m.p. 199°-201° C.

EXAMPLE 5

Control films were made without the addition of any UV blocker. These were made to determine baseline data for water content and extractables and to ascertain if the presence of an amine proton transfer agent would adversely affect the properties of the polymer. The initiators tested were: benzoin methyl ether (BME), benzophenone (BP) and benzil (BZ). The amine proton transfer agent was triethanolamine (TEA). The control set of films were prepared using siliconized glass plates with three tape thickness spacers. They were cured for two hours under 40 watt fluorescent black lights (F40T12/BLB), which were situated 4" away from the films. For determination of water content, the films were weighed, hydrated by boiling in distilled water for four hours and weighed after removing excess surface water. To determine extractables, the hydrated films were dried overnight at 80° C. under vacuum and weighed. The other components of the films were: hydroxyethyl methacrylate (HEMA) 85 pts, ethylene glycol dimethacrylate (EGDMA) 0.34 pts, and glycerin 15 pts. The results are tabulated in Table I.

TABLE I

| Initiator (concentration, parts) | % $H_2O$ | % Extractables |
|---|---|---|
| BME (.17) | 39.9 | 21.7 |
| BME (.4) | 40.3 | 21.6 |
| BZ (.2) | 39.9 | 20.9 |
| BZ (.4) | 39.9 | 20.7 |
| BP (.2) | 39.4 | 23.3 |
| BP (.4) | 39.2 | 21.7 |
| BME (.2) TEA (.9) | 41.0 | 22.0 |
| BME (.4) TEA (1.8) | 42.0 | 23.6 |
| BZ (.2) TEA (0.6) | 40.1 | 20.6 |
| BZ (.4) TEA (2.2) | 41.6 | 23.6 |
| BP (.2) TEA (0.8) | 39.3 | 21.8 |
| BP (.4) TEA (1.2) | 39.1 | 22.1 |

From the above results it can be seen that all films cured and the properties of the films were not affected dramatically by amines. There was no evidence of discoloration in the films containing amines. It is quite likely that the water soluble TEA is removed from the film during the extraction process. The yellow color of BZ was barely detectable in the extracted films and did not seem objectionable.

EXAMPLE 6

Using the same cure conditions of Example 5, films were prepared containing 1% of the compound of Example 2 with BME and BZ+TEA as initiators. It was not necessary to measure water content or extractables to see that the inventive chloro compound markedly retarded the cure. The films were very soft and curled, indicating poor curing. This was to be expected since the light energy from "black flourescent" lamps is mainly in the region from 310 to 400 nm., the region very effectively blocked by the inventive compounds.

EXAMPLE 7

Films having the compositions shown in Table II below were prepared, most of which contained the inventive chloro compound. A 400 watt water cooled medium pressure mercury "sun lamp" with a plain glass aperture placed 12 inches away was used to cure these films. This light source provided considerable energy with wavelengths greater than 380 nm. The water cooling system also filtered out sufficient infrared radiation so that the temperature of the films did not rise above 25° C. The properties of the films were determined as in Example 5 and are listed below in Table II.

minutes to give a reasonably cured film. The film curled severely on hydration, indicative of differential curing through the film. This appears to be caused by the increasing amount of UV absorption by the blocking agent as the light passes through the film. In films with 1% UV blocker, no cure was observed after up to 90 minutes.

BP, in the presence of 0.5% of the inventive chloro compound, did not give cured films, even with a proton transfer agent. BDME in the presence of 0.5% of the inventive chloro compound gave cured films with less curling than the BME initiated films. Cures were obtained under varying degrees of time and intiator concentration with BZ and MDEA as a proton transfer agent. However, the curling phenomenon was still evident indicating differential curing. The films made with TXN and MDEA gave the shortest minimum cure time and little or no curling of the films was observed. The improved cure over that observed for the other initiators is undoubtedly due to the much stronger absorption of light above 350 nm. by TXN.

EXAMPLES 8-13

Films were prepared according to the procedure of Example 7. Each film contained 85 pts HEMA, 0.34 pts

TABLE II

| Initiator (pst) | Pts MDEA | Pts inventive chloro compound | Cure Time min. | % $H_2O$ | % Extract. | Comments |
|---|---|---|---|---|---|---|
| BP (.2) | 0.4 | 0.5 | 15,45,120 | — | — | Not cured |
| BME (.17) | — | — | 15 | 43 | 22 | |
| " | — | — | 30 | 42 | 24 | |
| " | — | — | 45 | 41 | 24 | |
| " | — | 0.5 | 30 | — | — | Not cured |
| " | — | 0.5 | 45 | 41 | 50 | Partial cure |
| " | — | 0.5 | 60 | 40 | 25 | Severe curling |
| " | — | 0.5 | 90 | 39 | 22 | " |
| " | — | 1.0 | 40,60,90 | — | — | Not cured |
| BDME (.2) | — | 0.5 | 60 | 40 | 24 | Moderate curling |
| " | — | 0.5 | 90 | 43 | 24 | " |
| " | — | 0.5 | 120 | 38 | 21 | " |
| BZ (.2) | 0.4 | — | 15 | 43 | 23 | |
| " | 0.4 | — | 30 | 46 | 30 | |
| " | 0.4 | — | 45 | 41 | 24 | |
| " | 0.4 | 0.5 | 30 | — | — | Not cured |
| " | 0.4 | 0.5 | 45 | 41 | 26 | Moderate curling |
| " | 0.4 | 0.5 | 60 | 42 | 28 | " |
| " | 0.4 | 0.5 | 90 | 41 | 21 | " |
| " | 0.4 | 0.5 | 120 | 44 | 22 | " |
| " | 0.8 | 0.5 | 60 | 40 | 24 | " |
| " | 0.8 | 0.5 | 90 | 42 | 22 | " |
| " | 0.8 | 0.5 | 120 | 43 | 22 | " |
| BZ (.4) | 0.8 | 0.5 | 60 | 42 | 28 | " |
| " | 0.8 | 0.5 | 90 | 41 | 21 | " |
| " | 0.8 | 0.5 | 120 | 44 | 22 | " |
| BZ (.2) | 0.4 | 1.0 | 60 | 42 | 28 | " |
| " | 0.4 | 1.0 | 90 | 41 | 21 | " |
| " | 0.4 | 1.0 | 120 | 44 | 22 | " |
| TXN (.2) | 0.4 | 0.5 | 30 | 40 | 21 | No curling |
| " | 0.4 | 0.5 | 60 | 39 | 21 | " |
| " | 0.4 | 0.5 | 90 | 39 | 21 | " |
| " | 0.8 | 0.5 | 15 | 40 | 21 | Slight curling |
| " | 0.8 | 0.5 | 30 | 43 | 19 | No curling |
| " | 0.8 | 0.5 | 60 | 41 | 19 | " |
| " | 0.8 | 0.5 | 90 | 44 | 19 | " |

BDME = benzildimethylketal
MDEA = methyldiethanolamine
TXN = thioxanthen-9-one

BME was used both with and without inventive UV blocker to generate baseline data. The films without the UV blocker had water contents and extractables that were somewhat high, but comparable to those found for films of Example 5 (see Table I). In the presence of 0.5% UV blocker, BME required a minimum of 60

EGDMA, 15 pts glycerin, 0.5 pts of the inventive chloro compound, and an initiator. The particular initiators used in Examples 8-13 are shown below in Table III and the properties of the resulting films are tabulated below in Table IV.

TABLE III

| Example | Initiator |
|---|---|
| 8 | 0.2 pts BME |
| 9 | 0.2 pts TXN + 0.4 pts MDEA |
| 10 | 0.2 pts TXN + 0.4 pts MDEA |
| 11 | 0.3 pts TXN + 0.3 pts MDEA |
| 12 | 0.1 pts TXN + 0.2 pts MDEA |
| 13 | 0.2 pts TXN + 0.8 pts MDEA |

TABLE IV

| Example | Cure Time Min. | Modulus | Tensile | % Elong. | Tear Init. |
|---|---|---|---|---|---|
| 8 | 120 | 56.2 | 60.4 | 201 | 5.9 |
| 9 | 30 | 46.6 | 36.4 | 304 | 6.5 |
| 10 | 60 | 43.8 | 42.3 | 202 | 5.9 |
| 11 | 30 | 58.1 | 53.7 | 227 | 5.0 |
| 12 | 30 | 60.1 | 72.2 | 269 | 5.5 |
| 13 | 30 | 56.6 | 44.4 | 160 | 4.1 |

| Example | Tear Prop. | % $H_2O$ | % Ext. | MeOH Ext. | $O_2$ Perm. X HEMA |
|---|---|---|---|---|---|
| 8 | 3.5 | — | — | — | — |
| 9 | 4.3 | 39.4 | 23.9 | 5.0 | 1.0 |
| 10 | 3.7 | 39.8 | 22.8 | 4.6 | 1.1 |
| 11 | 3.7 | 39.6 | 19.3 | — | 1.0 |
| 12 | 3.6 | 40.8 | 19.2 | — | 1.0 |
| 13 | 2.8 | — | — | — | 1.1 |

The results shown in Table IV are acceptable for use in producing contact lenses. There does not appear to be any obvious relationship between the properties of the films tested and the level of TXN or MDEA. Also the oxygen permeability of the films was not adversely affected by the change in cure.

EXAMPLE 14

A study of the UV absorption spectra of films of varying thickness (from 1–4 tapes) was carried out to determine how close to theoretical the observed UV absorption spectra of the films were. A representative film made from a monomer mix containing 0.5% of the inventive chloro compound with a hydrated thickness of 0.09 mm. was tested and the observed absorbance at 340 nm. of 0.98 agrees well with a calculated theoretical value of 1.06. The theoretical value was calculated using a 12% linear expansion value for the hydrated film, ignoring any contribution to the absorbance from residual TXN. A transmission spectrum for a similar hydrated film that was 0.08 mm. thick showed that the film absorbed 70% of the incident light between 300 and 400 nm. This region is the one which causes the most ocular damage. In addition, the cytotoxicity of films containing the inventive chloro compound at a concentration of 0.5% was also determined. Both hydrated and non-hydrated films were found to be non-cytotoxic.

EXAMPLE 15–20

Contact lenses were prepared by a conventional spin-casting method with a single spinner set-up, except that a 275 watt, water cooled mercury lamp with a plain glass aperture was used. The cure was done under nitrogen and the light was approximately 2″ from the lens mold. Each lens was made from 85 pts HEMA, 0.34 pts EGDMA, 15 pts glycerin, 0.5 pts of the inventive chloro compound and an initiator. Description of a typical preparation is as follows:

A 30 μl sample of the monomer mix was placed in a polyvinyl chloride (PVC) lens mold and the mold was rotated by hand to wet the entire surface with the monomer. The filled mold was placed in the spinning apparatus, which was closed and purged with nitrogen until the oxygen level was below 20 ppm. The mold was spun at 375 rpm. for at least 5 minutes and the shutter opened to admit the light. The cure time was typically 20 minutes. The mold was removed from the spinner and placed in a desiccator until the lens was released from the mold.

The degree of polymerization was estimated by a near infrared technique that measured residual vinyl groups. The results are tabulated in Table V.

TABLE V

| Example | Initiator Parts TXN | Parts MDEA | Est. Cure |
|---|---|---|---|
| 15 | 0.1 | 0.2 | 90–95% |
| 16 | 0.1 | 0.4 | 95% |
| 17 | 0.2 | 0.4 | 95% |
| 18 | 0.2 | 0.6 | 95% |
| 19 | 0.2 | 0.8 | 95% |
| 20 | 0.3 | 0.3 | 95% |

All lenses appeared to be completely cured except for Example 15.

Difficulties in dry releasing the lenses from the PVC molds prevented the determination of extractables and water content for a number of the lenses. Enough material was obtained from the set of wet released lenses in Example 19 to obtain the water content and refractive index, which were 38.9% and 1.434 respectively.

The most preferred initiator system for use in the present invention is TXN and MDEA. Other initiators and proton transfer agents may be used, however. For example, xanthone; 2-chlorothioxanthone; Michler's Ketone; 9,10-phenanthrenequinone; 9,10-anthraquinone; α,α-dimethoxy-α-phenyl acetophenone; α,α-diethoxyacetophenone; and 1-phenyl-1,2-propanedione-2-O-benzoyl oxime may be used as initiators, with xanthone and 2-chlorothioxanthone being preferred. Suitable proton transfer agents include alcohols, ethers and tertiary amines containing an α-hydrogen. Tertiary amines are the preferred proton transfer agents with MDEA, TEA, and dimethylethanolamine being the most preferred tertiary amines.

In general, the UV absorbing composition should be present in the contact lens in an amount sufficient to absorb a substantial portion of the UV light that impinges on the lens. In most cases, about 0.25% up to about 2% by weight of the UV absorbing composition is sufficient. Preferably from about 0.4% to about 0.5% of the UV absorbing composition is incorporated into the contact lens, which may be of the corneal, scleral or intraocular type.

EXAMPLE 21

Two −3.00 U4 Bausch & Lomb Soflens ® contact lenses were studied for ultraviolet and visible light transmission properties. One of the lenses contained 0.4% of the inventive methoxy compound, while the other lens contained no UV absorber. The percent transmission of the lenses at specific wavelengths were determined and the results are shown in Table VI.

TABLE VI

| Lens | % Transmission |
|---|---|
| without UV blocker | 99% at 500 nm. |
|  | 99% at 400 nm. |
| with UV blocker | 99% at 500 nm. |
|  | 95% at 400 nm. |

The percent transmission of the lenses were integrated over various spectral regions. The method used to calculate the values gave equal consideration to the transmission at each wavelength. Table VII below shows the results.

TABLE VII

| Light | Spectral Region (nm.) | Lens | % Transmission |
|---|---|---|---|
| visible | 800–400 | without UV blocker | 99 |
|  |  | with UV blocker | 99 |
| UV | 400–300 | without UV blocker | 98 |
|  |  | with UV blocker | 33 |
| UV | 300–200 | without UV blocker | 48 |
|  |  | with UV blocker | 11 |

The resulting lens with incorporated UV blocker showed no yellowing to the naked eye. Also the UV absorbing properties of this lens appear to be superior to the known UV absorbing contact lenses in that less UV blocking compound is required to give the same degree of UV absorption in the 300–400 nm. range of light. The novel UV absorbing compounds shown below are believed to exhibit the same desirable properties as the chloro and methoxy compounds discussed above.

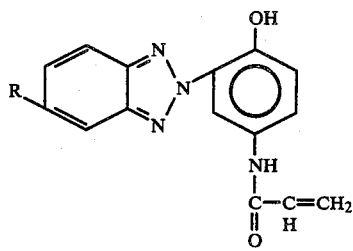

EXAMPLE 22

Synthesis of 2-(2-hydroxy-5-aminophenyl)-5,6-methylenedioxybenzotriazole

A sample of 4,5-methylenedioxy-2-nitroaniline is diazotized and coupled with p-acetamidophenol according to the procedure described in Example 1. The dark red azo dye which is obtained is collected by filtration and reduced with sodium dithionite and base to give 2-(2-hydroxy-5-aminophenyl)-5,6-methylenedioxybenzotriazole.

EXAMPLE 23

Synthesis of 2-(2-hydroxy-5-methacrylamidophenyl)-5,6-methylenedioxybenzotriazole According to the procedure of Example 2, a sample of 2-(2-hydroxy-5-aminophenyl)-5,6-methylenedioxybenzotriazole is treated with methacryloyl chloride in the presence of triethylamine to yield 2-(2-hydroxy-5-methacrylamidophenyl)-5,6-methylenedioxybenzotriazole. The corresponding chloro, methoxy and methylenedioxy compounds of the acrylamidophenyl series may be produced according to the general synthetic routes disclosed above for the corresponding methacrylamidophenyl compounds.

The foregoing specification has emphasized certain preferred embodiments of the present invention. Nevertheless, other embodiments not specifically described may fall within the spirit and scope of the present invention.

We hereby claim as our invention:

1. In a contact lens comprising a polymer formed by copolymerizing a first monomer suitable for use in making such lenses and a copolymerizable monomeric ultraviolet absorber, the improvement which comprises employing as the monomeric ultraviolet absorber about 0.25 to about 2% by weight of a compound selected from the group of compounds having the formula:

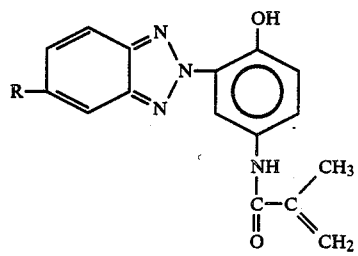

wherein R is Cl or OCH$_3$.

2. The contact lens of claim 1 wherein R is Cl.
3. The contact lens of claim 1 wherein R is OCH$_3$.
4. The contact lens of claim 1 wherein said first monomer is hydroxyethyl methacrylate.
5. The contact lens of claim 1 additionally comprising glycerin.
6. The contact lens of claim 1 additionally comprising ethylene glycol dimethacrylate.
7. The contact lens of claim 1 wherein said compound is present in said lens in an amount between about 0.4% and about 0.5% by weight.
8. The contact lens of claim 1 wherein said lens is of the corneal, scleral or intraocular type.
9. The contact lens of claim 1 wherein said lens is a soft corneal contact lens.

* * * * *